United States Patent
Lenna et al.

(10) Patent No.: US 9,562,068 B2
(45) Date of Patent: Feb. 7, 2017

(54) PROCESS FOR THE PREPARATION OF 7 α-(METHOXYCARBONYL)-3-OXO-17ALPHA-PREGN-4,9(11)-DIEN-21,17-CARBOLACTONE, A USEFUL INTERMEDIATE FOR THE SYNTHESIS OF MOLECULES WITH PHARMACOLOGICAL ACTIVITY

(71) Applicant: INDUSTRIALE CHIMICA S.R.L., Milan (IT)

(72) Inventors: Roberto Lenna, San Giorgio su Legnano (IT); Riccardo Di Brisco, Trecate (IT); Francesco Barbieri, Bovisio Masciago (IT)

(73) Assignee: INDUSTRIALE CHIMICA, S.r.l. (IT)

( * ) Notice: Subject to any disclaimer, the term of this patent is extended or adjusted under 35 U.S.C. 154(b) by 0 days.

(21) Appl. No.: 14/885,861

(22) Filed: Oct. 16, 2015

(65) Prior Publication Data

US 2016/0108083 A1    Apr. 21, 2016

(30) Foreign Application Priority Data

Oct. 17, 2014    (IT) .............................. MI2014A1800

(51) Int. Cl.
*C07J 21/00*    (2006.01)

(52) U.S. Cl.
CPC .................... *C07J 21/003* (2013.01)

(58) Field of Classification Search
CPC ..................................................... C07J 21/003
USPC ......................................................... 540/44
See application file for complete search history.

(56) References Cited

FOREIGN PATENT DOCUMENTS

WO        02082895        10/2002

OTHER PUBLICATIONS

Sigma-Aldrich Co. LLC, N,N-Diethyl-1,1,2,3,3,3-hexafluoropropylamin, 2 pages, Jun. 22, 2015.
Takaoka et al., F-Propene-Dialkylamine Reaction Prodcuts as Fluorinating Agents, Bulletin of the Chemical Sociatey of Japan, vol. 52, pp. 3377-3380, Nov. 1979.
Italian Search Report and Written Opinion mailed on Jun. 22, 2015 for IT MI20141800 filed on Oct. 17, 2014.

*Primary Examiner* — Kahsay Habte
(74) *Attorney, Agent, or Firm* — Fish & Tsang, LLP

(57) ABSTRACT

An improved process for the preparation of intermediate (V) through the elimination of a molecule of water from intermediate (IV) is described.

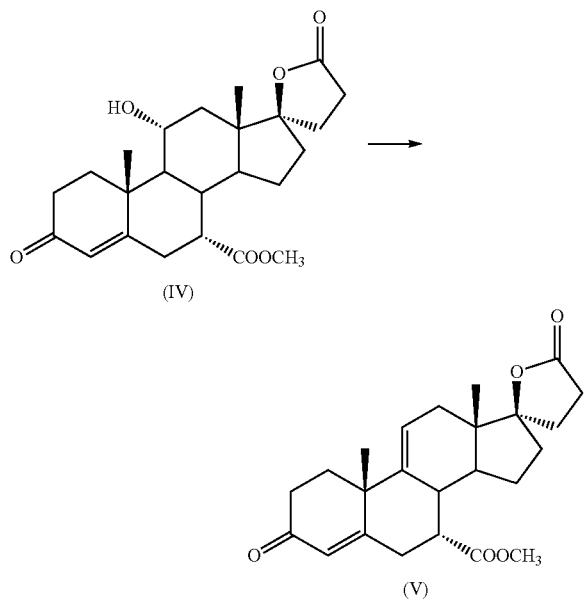

Intermediate (V) is a key molecule for the synthesis of eplerenone, a synthetic steroid with pharmacological activity used in the treatment of chronic pathological conditions, including hypertension.

3 Claims, No Drawings

PROCESS FOR THE PREPARATION OF 7 α-(METHOXYCARBONYL)-3-OXO-17ALPHA-PREGN-4,9(11)-DIEN-21,17-CARBOLACTONE, A USEFUL INTERMEDIATE FOR THE SYNTHESIS OF MOLECULES WITH PHARMACOLOGICAL ACTIVITY

FIELD OF THE INVENTION

The present invention relates to a process for the synthesis of the intermediate 7α-(methoxycarbonyl)-3-oxo-17α-pregn-4,9(11)-dien-21,17-carbolactone, having the following structural formula (V):

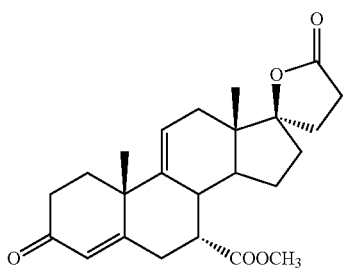

(V)

useful in the synthesis of eplerenone, having the following structural formula (II):

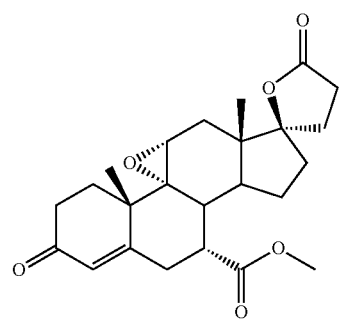

(II)

BACKGROUND ART

Eplerenone is a synthetic steroid with pharmacological activity as an aldosterone antagonist, whose excess in the human body is related to chronic pathological conditions including hypertension. This is not the first synthetic molecule with anti-aldosterone activity used in drug preparation but, unlike its predecessors, among which the most important is certainly spironolactone, it has a reduced hormonal activity. This characteristic leads to a decrease in undesired side effects on the endocrine system.

Eplerenone is disclosed in U.S. Pat. No. 4,559,332 of 1985.

The transformation object of the present application, the elimination of a molecule of water from intermediate (IV) to intermediate (V) depicted below

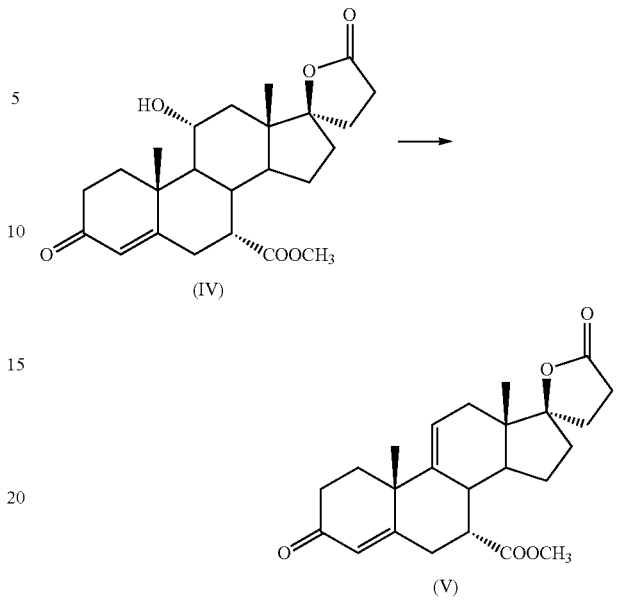

is described in WO 03/082895, in WO 98/25948 through the formation of reactive intermediates of hydroxyl in position 11 to be eliminated later on, and in WO 97/21720.

As can be easily checked in the experimental descriptions given in said patent applications, however, such reactions appear complex, burdened by the formation of considerable amounts of by-products.

Some of the examples of these documents provide no indication regarding yield and quality.

The reaction from intermediate (IV) to intermediate (V) is instead critical to the yield and the quality of the final eplerenone obtainable by oxidation of intermediate (V).

Therefore, the need to carry out the transformation from intermediate (IV) to intermediate (V) with a simple reaction, characterized by high yields and easily implemented on an industrial scale is felt.

SUMMARY OF THE INVENTION

The object of the present invention is to provide a new synthesis reaction of the intermediate 7α-(methoxycarbonyl)-3-oxo-17α-pregn-4-9(11)-dien-21,17-carbolactone (V) free from the drawbacks of the prior art.

According to the embodiment of the present invention, this object is achieved by the use of the mixture $(Et)_2NCF_2CHFCF_3/(Et)_2NFC=CFCF_3$, obtained by reacting diethylamine with hexafluoropropene, in which the two components are present in equivalent or approximately equivalent amounts, as described in detail hereinafter.

DETAILED DESCRIPTION OF THE PROCESS

The process of the invention is directed to the preparation of intermediate (V) by elimination of water from intermediate (IV) using as reagent the mixture (VI) $(Et)_2NCF_2CHFCF_3/(Et)_2NFC=CFCF_3$ obtained by reacting diethylamine with hexafluoropropene.

The content of the two components of mixture (VI) is determined with gas chromatographic analysis.

The amounts of the two components of mixture (VI) are variable in such ratios that the area of the minority component is not less than 75%, and preferably not less than 90%, than the area of the majority component.

The reaction solvent is a chlorinated pure solvent or a mixture of solvents containing at least one chlorinated solvent, inert under the reaction conditions, which solubilize intermediate (IV).

Preferably, methylene chloride and/or chloroform are used as chlorinated solvents.

The volume of solvent used is between 5 and 20 ml, preferably between 7.5 and 15 ml, per gram of the steroid used. The reaction temperature is between 0 and 45° C., preferably between 25 and 35° C.

The reaction time is between 12 and 48 hours, preferably between 24 and 36 hours.

The amount of reactive mixture (VI) used (v/w) is between 50 and 100% by volume, preferably between 50 and 75%, with respect to the weight of the reaction steroid.

EXAMPLES

The invention will be further described by the following examples.

The reagents and solvents used, unless otherwise stated, are commercially available from common suppliers of laboratory reagents such as Sigma-Aldrich, Fluka or equivalent.

The Ishikawa reagent used in Example 1, according to the manufacturers indications, consists by more than 90% of N,N-diethyl-1,1,2,3,3,3-hexafluoropropylamine.

The analytical controls by means of thin layer chromatography are carried out using Merck plates code 1.05554.0001.

GC checks are carried out by Agilent gas chromatograph model 7890A.

HPLC checks are carried out using Agilent chromatographs model 1290 Infinity and model 1200.

Example 1

Comparative

This example is representative of the reproduction of the example 18 of WO 03/082895.

5 g of 11α-hydroxy-7α-(methoxycarbonyl)-3-oxo-17α-pregn-4-ene-21,17-carbolactone (IV) are suspended in 15 mL acetonitrile at room temperature; 2.55 ml Ishikawa reagent (Aldrich 564990) are added, thus obtaining a suspension.

The mixture is heated to 60° C. and after 2.5 hours, the progress of the reaction is checked by TLC: no reaction.

Additional 15 ml acetonitrile and 2.55 ml Ishikawa reagent (Aldrich 564990) are added.

The system is kept at 60° C. and after 1 hour, the progress of the reaction is checked by TLC: minimum formation of intermediate (V), starting intermediate (IV) largely prevalent.

Example 2

5 g of 11α-hydroxy-7α-(methoxycarbonyl)-3-oxo-17α-pregn-4-ene-21,17-carbolactone (IV) are suspended in 15 mL acetonitrile at room temperature; 2.55 ml Ishikawa reagent (Aldrich 564990) are added, thus obtaining a suspension.

The mixture is heated to 60° C. and after 2.5 hours, the progress of the reaction is checked by TLC: no reaction.

5 ml methylene chloride (capped reaction flask) are added, thus obtaining a clear solution after 30 minutes.

After 1 additional hour of reaction, the system is cooled to 25° C. checking the progress of the reaction by TLC: minimum formation of intermediate (V), starting intermediate (IV) largely prevalent.

It is left under stirring for 16 hours at 20-25° C. obtaining, after 16 hours, the disappearance of the starting intermediate (IV) with the formation of intermediate (V) plus other stains in the TLC.

The reaction is quenched by adding methanol first and then 15 ml of a basic aqueous solution of water-sodium bicarbonate with pH=8 to the reaction mixture.

The organic fraction is removed by distillation at reduced pressure obtaining a solid (6 g) whose content of intermediate (V), as determined by HPLC analysis, is equal to 3.47 g, corresponding to a yield of 72.5%.

The product is placed under stirring for 10 hours in methyl tert butyl ether (25 ml) at 25° C.

After filtration and drying, 3.5 g of solid are obtained.

The content of intermediate (V) of this solid, as determined by HPLC analysis, is equal to 3.1 g, corresponding to a yield of 66%.

Example 3

10 g of 11α-hydroxy-7α-(methoxycarbonyl)-3-oxo-17α-pregn-4-ene-21,17-carbolactone (IV) are suspended in 100 mL chloroform at room temperature; 5.1 ml of reagent (VI) are added.

The mixture is stirred at 30° C., checking the progress of the reaction by TLC after 30 hours: reaction ended.

The reaction is quenched by adding methanol first and then 30 ml of a basic aqueous solution of water-sodium bicarbonate with pH=8 to the reaction mixture.

The phases are separated, the organic fraction is eliminated by distillation at reduced pressure, obtaining a yellow solid which is dried at T=45° C. at reduced P to constant weight (9.93 g); the solid is of suitable quality to be used for the next steps.

The content of intermediate (V), as determined by HPLC analysis, is equal to 8.63 g, corresponding to a yield of 90%.

Example 4

This example is representative of the production of reaction mixture (VI).

At room temperature, 100 ml dichloromethane and 17.7 ml diethylamine are loaded in a flask.

It is cooled to T=−10° C. and, under stirring, 32.5 g hexafluoropropene are made to be absorbed by the solution over 10 hours.

The GC check shows the complete disappearance of diethylamine from the reaction mixture.

Dichloromethane is distilled at reduced pressure obtaining 33.7 g of reactive mixture (VI) which at the GC check shows the virtually exclusive presence of the two fluorinated components with 49.94 and 48.46% areas.

Such a mixture can be used as such without need for subsequent purifications.

What is claimed is:

1. A process for the production of 7α-(methoxycarbonyl)-3-oxo-17α-pregn-4-9(11)-dien-21,17-carbolactone (V) comprising elimination of a molecule of water from 11α-hydroxy-7α-(methoxycarbonyl)-3-oxo-17α-pregn-4-en-21,17-carbolactone (IV) by reaction with a two component mixture (VI) consisting of $(Et)_2NCF_2CHFCF_3$ and $(Et)_2NFC=CFCF_3$, wherein quantities of the two components of said mixture (VI) are variable in ratios such that an observed area of a minority component is not less than 75% than an observed area of a majority component as determined in a gas chromatographic analysis.

2. The process according to claim 1, wherein the amounts of the two components of said mixture (VI) are variable such that an observed area of a minority component is not less than 75% than an observed area of a majority component as determined in a gas chromatographic analysis.

3. The process according to claim 1, in which the elimination of a molecule of water is realized by treating the intermediate (IV) with the mixture (VI) in a chlorinated solvent or in a mixture of solvents in which at least one of the components is a chlorinated solvent.

* * * * *

UNITED STATES PATENT AND TRADEMARK OFFICE
CERTIFICATE OF CORRECTION

PATENT NO. : 9,562,068 B2  
APPLICATION NO. : 14/885861  
DATED : February 7, 2017  
INVENTOR(S) : Roberto Lenna Page 1 of 1

It is certified that error appears in the above-identified patent and that said Letters Patent is hereby corrected as shown below:

In the Claims

In Claim 2 at Line 3 change "75%" to -- "90%" --

Signed and Sealed this  
Fifth Day of December, 2017

Joseph Matal  
*Performing the Functions and Duties of the*  
*Under Secretary of Commerce for Intellectual Property and*  
*Director of the United States Patent and Trademark Office*